(12) United States Patent
Weerman

(10) Patent No.: US 8,271,540 B2
(45) Date of Patent: Sep. 18, 2012

(54) COMPUTER ASSISTED DATA COLLECTION FOR SURVEYS AND THE LIKE

(75) Inventor: Albert Weerman, Topanga, CA (US)

(73) Assignee: The Rand Corporation, Santa Monica, CA (US)

(*) Notice: Subject to any disclaimer, the term of this patent is extended or adjusted under 35 U.S.C. 154(b) by 1019 days.

(21) Appl. No.: 11/415,913

(22) Filed: May 1, 2006

(65) Prior Publication Data

US 2006/0265348 A1    Nov. 23, 2006

Related U.S. Application Data

(60) Provisional application No. 60/696,620, filed on Jul. 1, 2005, provisional application No. 60/682,204, filed on May 17, 2005.

(51) Int. Cl.
G06F 17/30    (2006.01)
(52) U.S. Cl. ........................................... 707/803
(58) Field of Classification Search .......... 707/100, 707/104.1, 103 R, 103 Y, 103 X, 103 Z, 803; 715/222; 705/10
See application file for complete search history.

(56) References Cited

U.S. PATENT DOCUMENTS

| | | | |
|---|---|---|---|
| 6,072,953 A | 6/2000 | Cohen et al. | |
| 6,442,663 B1 | 8/2002 | Sun et al. | |
| 7,475,339 B2 * | 1/2009 | Holloway et al. | 715/237 |
| 8,086,648 B2 * | 12/2011 | Weerman | 707/803 |
| 2002/0035486 A1 | 3/2002 | Huyn et al. | |
| 2003/0154406 A1 * | 8/2003 | Honarvar et al. | 713/201 |
| 2003/0198934 A1 * | 10/2003 | Sendowski et al. | 434/350 |
| 2004/0049683 A1 * | 3/2004 | Abraham-Fuchs | 713/182 |
| 2007/0282664 A1 * | 12/2007 | Monster | 705/10 |

OTHER PUBLICATIONS

Danmark Statistik, Proceesdings of the 8th International Blaise Users Conference, May 2003, pp. 1-330.*
Statistics, Netherlands; Blaise, A short description of the current status; Feb. 2007; pp. 1-20.*
Foreign Search Report dated Feb. 8, 2010 from related European application No. 06759996.9.
PCT International Search Report dated Oct. 5, 2007 for related PCT application No. PCT/US06/19033.

(Continued)

*Primary Examiner* — Sheree Brown
(74) *Attorney, Agent, or Firm* — Foley & Lardner LLP

(57) ABSTRACT

An exemplary MMIC ("Multi-Mode Interviewing Capability") survey program is a computerized tool that supports various traditional modes of collecting interview data, including telephone interviewing, written interviewing, and personal interviewing, and can be used to manage the whole interview process from questionnaire design, sample management, and fieldwork monitoring to final dataset production. The collected data may also include non-textual data from survey participants such as medical measurements of blood pressure and heart rate. Self-interviewing using the Internet is also possible which permits real time availability of results and the participation of respondents from virtually anywhere in the world, using devices such as PDA's, Smart phones and Web TV's. The MMIC survey structure is non-linear and object oriented, which permits a connection between all the building blocks of the survey to be defined on any level. The compiled survey includes sufficient metadata to facilitate decompilation and the production of equivalent source code in any supported programming language, whether or not it was originally programmed in that language. This stored metadata not only allows researchers to later trace back the exact conditions under which this particular answer was given, but also permits results from multiple iterations of the related surveys to be combined in a rigorous manner that will be transparent to subsequent analysis and research.

36 Claims, 11 Drawing Sheets

OTHER PUBLICATIONS

US Office Action dated Aug. 20, 2010 from related U.S. Appl. No. 12/479,451.
Danmark Statistik, Proceedings of the 8th International Blaise Users Conference, May 2003, pp. 1-330.
US Office Action dated Feb. 1, 2011 from related U.S. Appl. No. 12/479,451.
Office Action dated Jun. 1, 2011 from related U.S. Appl. No. 12/479,451.

* cited by examiner datamodel example "This is an example questionnaire"

fields — 48 q1 "Do you have a dog?"/"dogquestion":(no, yes)

q2 "What is its name?"/"dogname". string rules — 50 q1 if q1 = yes then q2 endif endmodel

FIG. 5
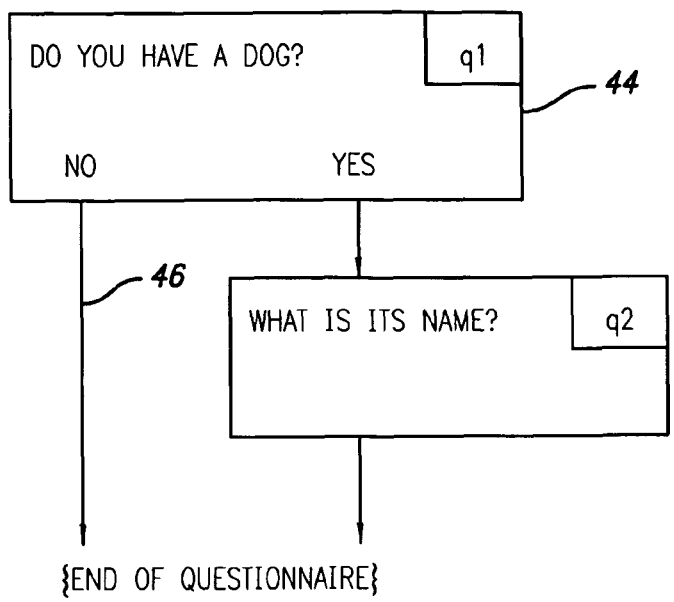
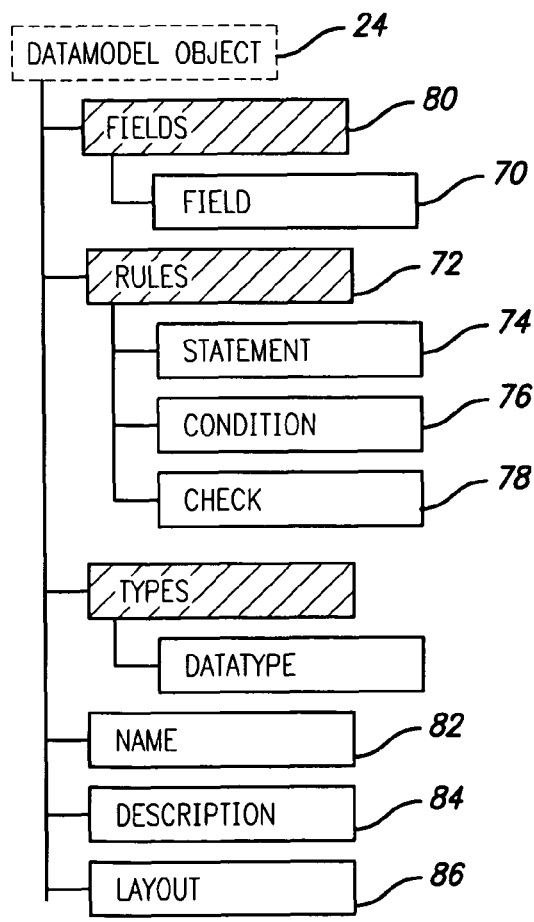
FIG. 11

```
datamodel fillexample
languages =      {this questionnaire has two languages defined, English
and Spanish}
   ENG "Self interviewing - English",
   SPN "Self interviewing - Spanish"
type                  {types are global data types}
  TYesNo = (yes "Yes" "Si",
       no "No" "No" )
  TGender = (male   "Male"   "Masculino",
          female "Female" "Femenino")
procedure HWPfill       {this procedure returns a value based on the marriage
and gender questions}
parameters            {the prodedure accepts two import parameters and
exports a strig}
   import piMarried: TYesNo
   import piGender: TGender
   export peFLHWP: string
rules
  if piMarried = yes then
    if piGender = male then
       if activelanguage = ENG then
  peFLHWP:='(and your wife)'    (married, male and English language)
  else
  peFLHWP:='(y de su esposa)'   (married, male and Spanish language)
  endif
else
  if activelanguage = ENG then
  peFLHWP:='(and your husband)'(married, female and English language)
  else
  peFLHWP:='(y de su esposa)'      (married, female and Spanish language)
  endif
endif
else
   peFLHWP:= ' '   {this person is not married. The fill in q3 will be empty!}
  endif
endprocedure
fields
q1 "Are you married?" "¿ Es usted casado?": TYesNO
q2 "What is your gender?" "¿ cual es su sexo?":TGender
HWP: string     {this field is not used as an actual question but as a
reference in q3 question text}
   q3 "Do you^HWP have a dog?" "¿ Tiene ^HWP usted un perro?": TYesNo
rules
q1                  {ask question about marriage}
q2                  {ask question about gender}
HWPfill (q1, q2, HWP) {call HWPfill function to get the right question text for q3}
q3                  {ask question about dog}
endmodel
```

FIG. 14

COMPUTER ASSISTED DATA COLLECTION FOR SURVEYS AND THE LIKE

This application claims priority of U.S. provisional patent applications 60/682,204 and 60/696,620 filed on May 17, 2005, and Jul. 1, 2005, respectively, which are hereby incorporated by reference in their entirety.

FIELD OF INVENTION

The present invention relates generally to computer-assisted interviewing and other survey-oriented data collection technology. More specifically, an exemplary embodiment of the present invention includes a suite of computerized tools for managing an entire interview process from questionnaire design, sample management, and fieldwork monitoring to final dataset production and analysis.

BACKGROUND OF THE INVENTION

Blaise® [see http://www.cbs.nl/en/service/blaise/introduction.htm] is a computer-assisted interviewing (CAI) system and survey processing tool for the Windows® operating system. The system was developed by Statistics Netherlands and has been designed for use in official statistics. It is available to National Statistical Institutes and related research institutes. C2B (CentERdata to Browser) [see http://www.u-vt.nl/centerdata/en] is an add-on to the Blaise product which facilitates publication of a Blaise questionnaire to the Internet. using a 'standard' Blaise questionnaire. CASES [see http://cases.berkeley.edu] is a software package for collecting survey data based on structured questionnaires in both governmental and private sectors. Survent [see: http://www.cfm-c.com] is a system for computer-assisted telephone interviewing (CATI) which provides complete capabilities for designing, administering, and managing all of the complexities of sophisticated telephone-based research operations. SPSS [see http://www.spss.com] is a statistical software package for analyzing numeric data and for producing graphical representations of data.

These and other known survey tools typically utilize proprietary structures and programming languages that are relatively complex for the limited functionality which they support. Thus the programmer and the researcher have only limited control over the survey design, and only limited capability for analyzing the results and possible modifications to the questionnaire design as the survey is being conducted. Moreover, especially for large, recurring surveys involving many questions and many participants, relatively large development times are required, translation of the survey text into other languages is cumbersome, and the survey documentation is not presented in a format which is understandable to other than a trained programmer having extensive experience with that particular programming language.

SUMMARY OF THE INVENTION

In one presently preferred embodiment (hereinafter designated "MMIC"), there have been implemented a number of major improvements to the conventional questionnaire structure. This MMIC structure is non-linear and object oriented, which permits a connection between all the building blocks of the survey to be defined on any level. Fills used in question texts point to basic Field Object blocks, including explicit links to all the conditions used for that specific Field Object as well as links to all the statements assigned to a Field Object. This makes it possible to retrieve all the possible fills for any given Field Object, which in turn permits the MMIC Engine to have full control over the meta data at design time and not only at run time.

A second improvement as implemented in that preferred embodiment is the ability to recreate new source files based on the compiled MMIC objects. At any time, a compiled MMIC Datamodel Object can be decompiled to produce source code in any supported programming language, whether or not it was originally programmed in that language. This has the added advantage that you do not necessarily have to design or modify a questionnaire using a formal programming language.

Another improvement as implemented in the currently preferred embodiment is that the MMIC Datamodel Object is aware of all the routing and other functional connections between the different building blocks and can display the statements and conditions related to the current question while the interview is in progress, which enables a programmer to debug the source code faster and with more accuracy. The programmer is also able to assign watches to all necessary fields so that these related statements and conditions can be viewed at real time during debugging.

BRIEF DESCRIPTION OF THE FIGURES

For a fuller understanding of the principles underlying the present invention, and how its various aspects can be put to practical use, reference is made to the appended drawings, in which:

FIG. 5 shows how the questionnaire of may appear in a graphical user interface;

FIG. 11 shows certain structures of an exemplary MMIC Datamodel Object;

FIG. 14 shows the source code for an exemplary MMIC question constructed from a Fill in a Question Text.

DETAILED DESCRIPTION OF CERTAIN EMBODIMENTS

The present invention potentially encompasses a number of embodiments of varying functionality and complexity which may be used in various combinations and subcombinations to satisfy different needs of different users. Accordingly, although only a few examples of certain preferred embodiments of the present invention will be described in detail, it will doubtless be apparent to those skilled in the art how other combinations and subcombinations of the described embodiments may be used in other environments to satisfy the needs of other users.

Figure 1:
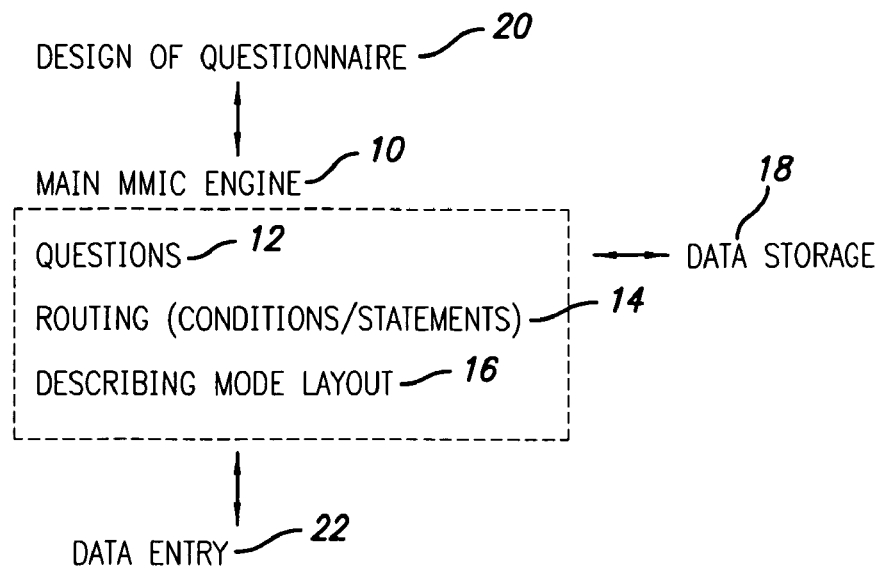
FIG. 1 shows an overview of an exemplary MMIC Engine.

FIG. 1 show a functional overview of an exemplary Engine 10 having a "multi-mode interviewing capability" ("MMIC"). This MMIC survey program is intended to support multiple methods of designing a questionnaire ("Data Model"), via a Programming Interface which preferably is capable of communicating with the programmer in various languages (such as Blaise, CASES, and native MMIC) and display modes (such as Text, Web or Graphic User Interface ("GUI")), and which will be described in more detail later in this document. In the Data Model design phase, the main MMIC Engine 10 is informed what questions 12 are being asked, in what order 14, and in what Database format and Layout 16. This information forms a Data Model, which is processed in the main MMIC Engine 10 and stored (together with any responses via the Interview Interface) in a separate data storage module 18. Once designed, the data entry part 22 of the process is able to retrieve these Question Texts 12 and routing 14, displaying questions in a number of different formats and modes. The MMIC survey program preferably supports a number of alternative computer assisted interviewing modes, including but not limited to CATI (Computer Assisted Telephone Interviewing) and CAPI (Computer Assisted Personal Interviewing).

MMIC Design

Figure 2:
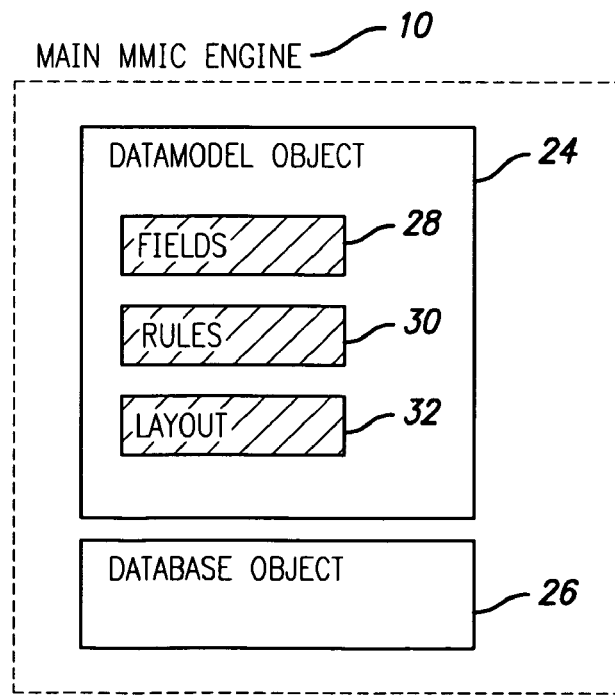
FIG. 2 shows how the MMIC Engine of FIG. 1 includes two basic building blocks. The Datamodel Object and the Database Object.

As shown in FIG. 2, the main MMIC Engine 10 consists of two basic building blocks: the Datamodel Object 24 and the Database Object 26.

The Datamodel Object 24 holds the structure for the entire questionnaire. It stores the questions (in the form of Field Objects 28) to be asked in the questionnaire and the order (in the form of Rules 30) in which they are asked. Datamodel Object 24 also stores Layout Objects 32 which determine the manner in which the various Field Objects 28 appear to the interviewer and/or respondent. The structure of the various MMIC Datamodel Objects are described in more detail hereinafter with respect to FIG. 11, FIG. 12, and FIG. 13.

Figures 3, 4:
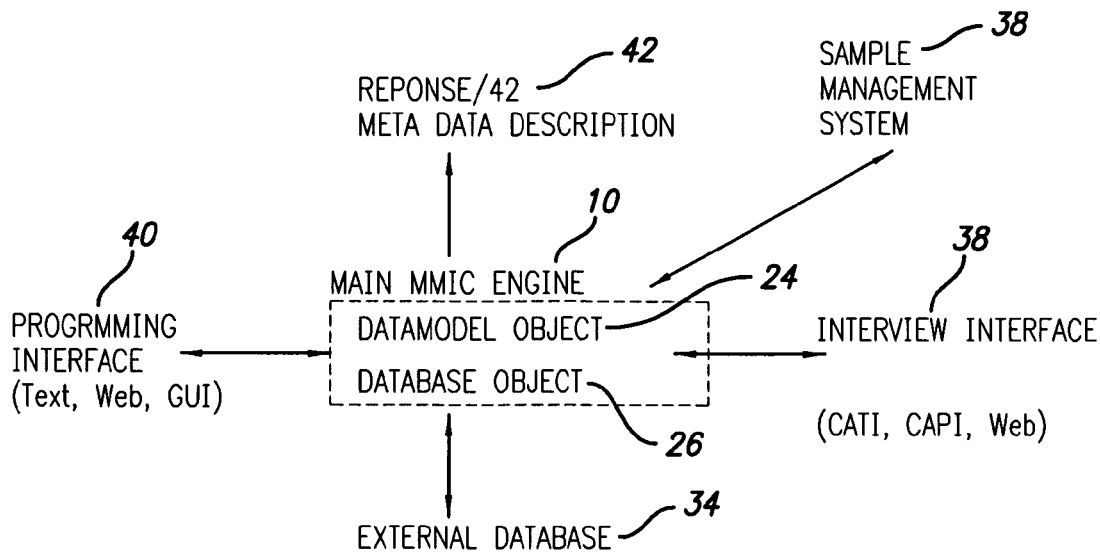
FIG. 3 shows an overview of MMIC and external programs.
FIG. 4 shows an example of a short MMIC program (written in the Blaise programming language) which defines an exemplary MMIC questionnaire.

FIG. 3 shows an overview of MMIC and external programs. In order to facilitate these external programs and usages, the MMIC survey system is setup in a modular or object oriented fashion. All internal components are connected to each other. The Database Object 26 communicates (retrieves and stores information) with an external third party database 34 such as Oracle, dBase or mySQL. The Database Object 26 is only pointing to referenced data stored in the third party database and is not holding the actual data. The third party database stores not only a participant's response, but also the context such as the date and time of each entry, the language in which this question was asked, the interviewing mode (web interview, telephone interview, etc.) and the version of the questionnaire in which the question was asked.

Other related utility programs may be provided such as a Sample Management System 36, an Interview Interface 38, a Programming Interface 40, and a Report module 42 which outputs Responses and Meta Data. These various utility programs 36, 38, 40, 42 are preferably external to the main MMIC Engine 10, but which collectively simplify the task of creating, running, and analyzing a survey under the overall management of the MMIC Engine.

Programming Interface

Programming of a MMIC questionnaire can be done in a number of ways and is preferably performed by means of an external Programming Interface 40. The researcher can use a programming language FIG. 4 a web interface, or a graphical user interface FIG. 5. The graphical user interface enables the user to click together a questionnaire by dragging and dropping boxes 44 for the questions 12, and arrows 46 for the routing 14, without needing to know a programming language. The primary function of the programming interface (whether it is a programming language, a web interface or a graphical user interface) is to fill the MMIC Engine Object 10 with information about the survey and the flow of the survey. The programming language describes all the questions 12 that can be asked in the survey, and the conditions 14 that determine what questions are going to asked and in what order. In case the survey is designed using a text-based programming language, the typed text is typically parsed and then assigned to the MMIC Datamodel Object. The parser is not part of the MMIC Datamodel Object but rather is included within the text-based portion of Programming Interface 40 and is only responsible for the interpreting the typed text by the programmer. The parser determines what parts of the typed text are Fields, Statements or Conditions (see FIG. 13) and assigns these parts to the MMIC Datamodel Object. The MMIC Datamodel Object has an internal compile function, which receives the parsed program text from the Programming Interface 40 and informs the user whether there are any errors in the programmed survey. These errors can be of different types. A user could forget to specify the answer possibilities to a question, or could make a mistake in a related Condition, for example, checking for a number although the question was designed to have only yes-no answer categories.

FIG. 4 shows an example of a short MMIC program (written in a Blaise-like programming language). The programmed questionnaire has two questions. The first question (q1) determines whether the second question (q2) is being asked. If someone answers yes to the question "Do you have a dog," the name of the dog is asked (q2). This short example shows the two important parts of the survey system: Fields and Rules. First the fields 44 are defined under the 'Fields' section 48 and later the routing 46 is defined under the 'Rules' section 50. The fields in this example are used as functions: they represent questions to be asked of the respondent, and accept input from the user.

Figure 6:
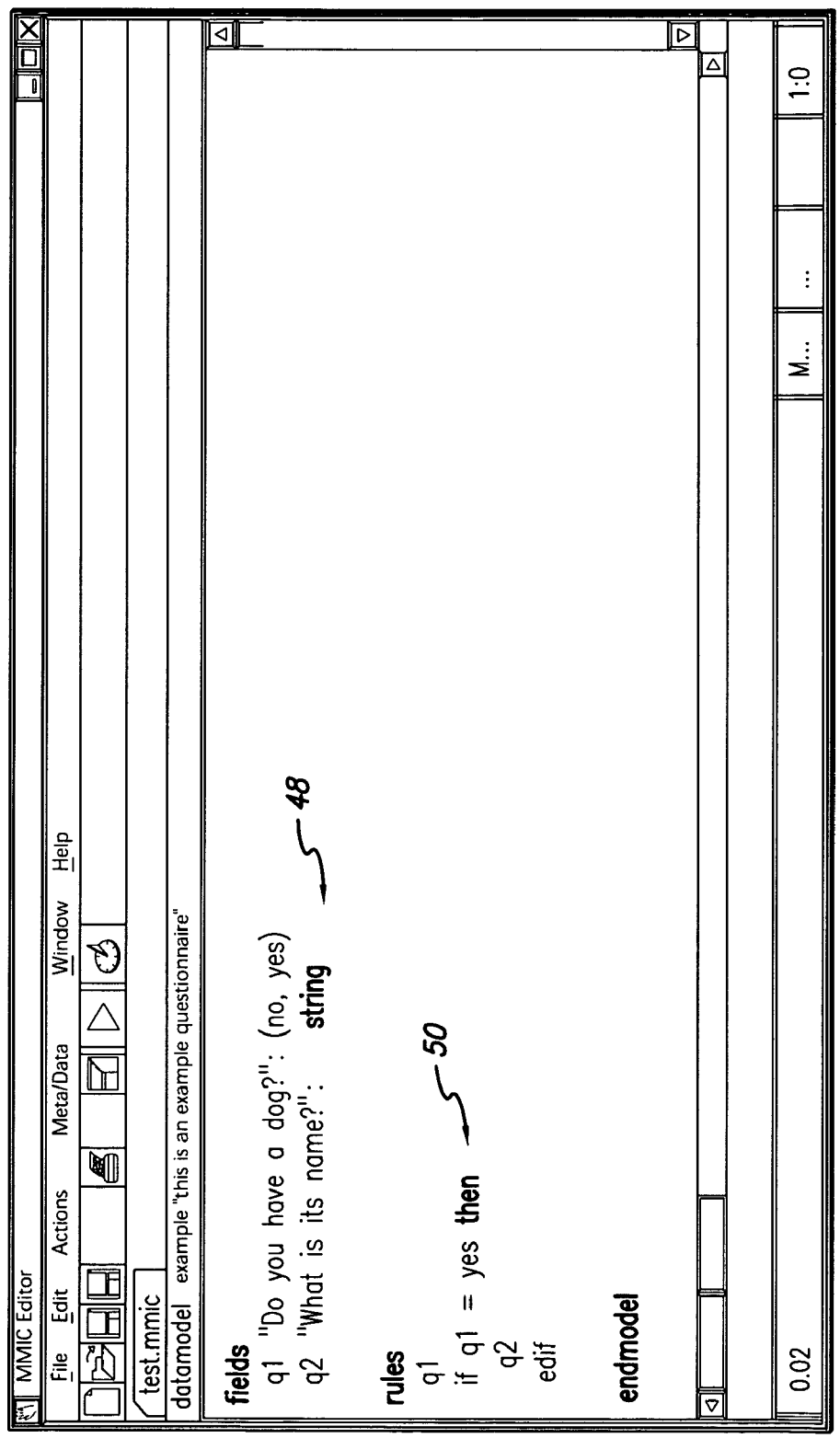
FIG. 6 is a screen dump of a typical MMIC programming environment.

As shown in FIG. 5, the same questionnaire will look a little different in the graphical user interface by means of which the researchers (or programmers) are able to design the questionnaire using graphic symbols such as arrows and boxes. FIG. 6 is a screen dump and shows how the same questionnaire will look in the MMIC programming environment. This environment is basically a text editor that uses syntax highlighting to make life easier for the programmer. Once a survey is programmed (in this case our simple dog example) a programmer can use the dropdown box under actions or the compile button on the top of the screen to compile the programmed questionnaire. In case of an error the programmer will be directed to the location in the source file where the problem or error occurred. After compiling the programmer can choose to run the survey in web or CAPI/CATI mode.

Interview Interface

Figure 7:
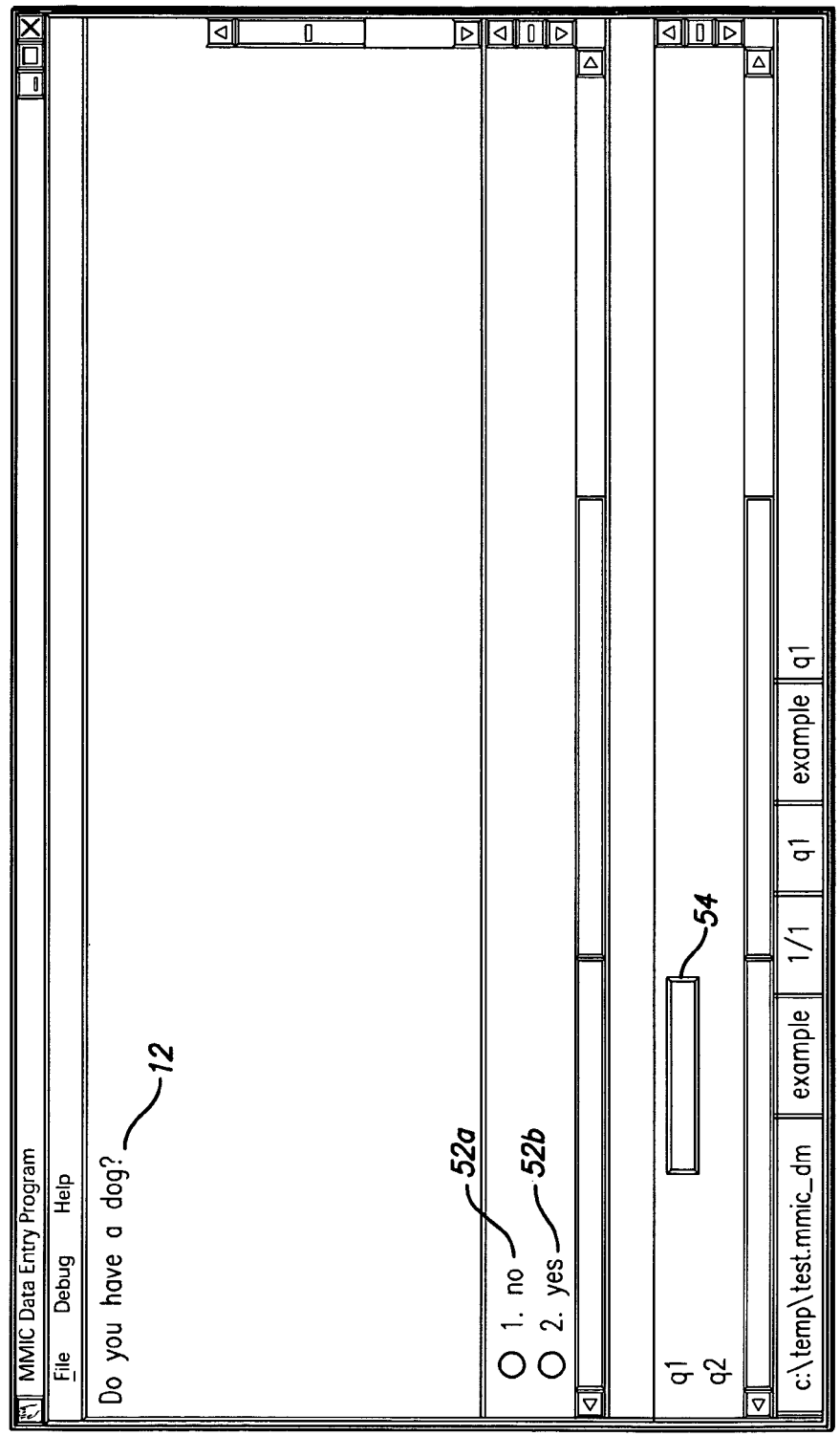
FIG. 7 is a screen dump of an exemplary CATI/CAPI environment for the MMIC survey system.
Figure 8:
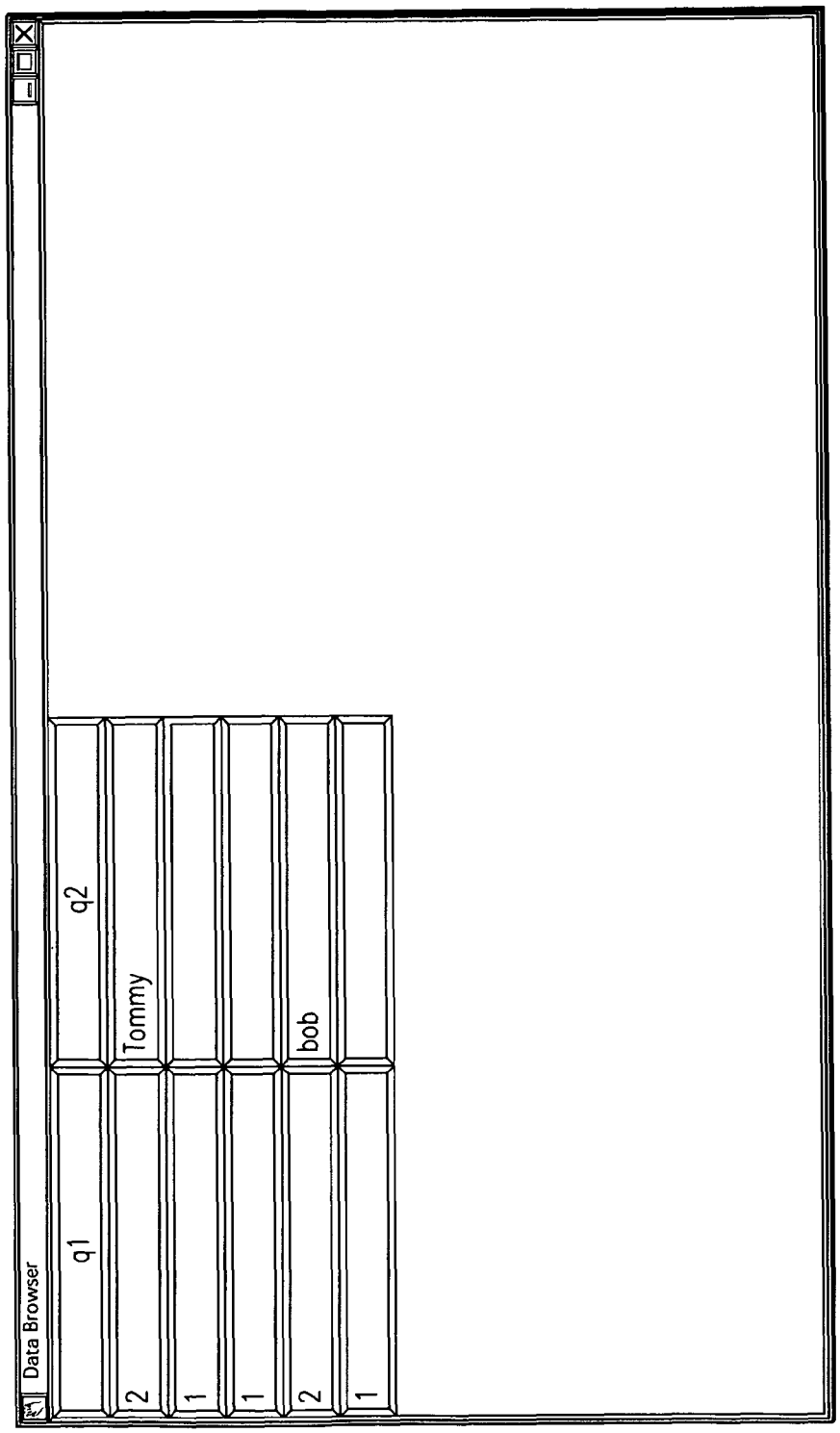
FIG. 8 is a screen dump showing an exemplary listing of completed records for a simple survey.

As shown in FIG. 7, the Interview Interface 38 consists of a data entry program capable of conducting web interviews, personal interviews and telephone interviews. In any of these interview modes, the interface typically presents the interviewer or respondent with a question 12 and allows the interviewer or respondent to enter an answer 52a, 52b to that question. Referring specifically to the screen dump of an exemplary CAPI/CATI environment for the MMIC survey system shown in FIG. 7, only the first question q1 on the route for our 'dog' survey is visible. In case the "yes" 52b branch is selected, the appropriate Question Text and edit box 54 for q2 will open on the bottom of the screen, allowing a interviewer or respondent to enter a name for the dog. FIG. 8 is a screen dump showing a simple listing of the completed records for this survey. Apparently only two of our respondents had dogs, one named Tommy and one named Bob.

Sample Management System

Figure 9:
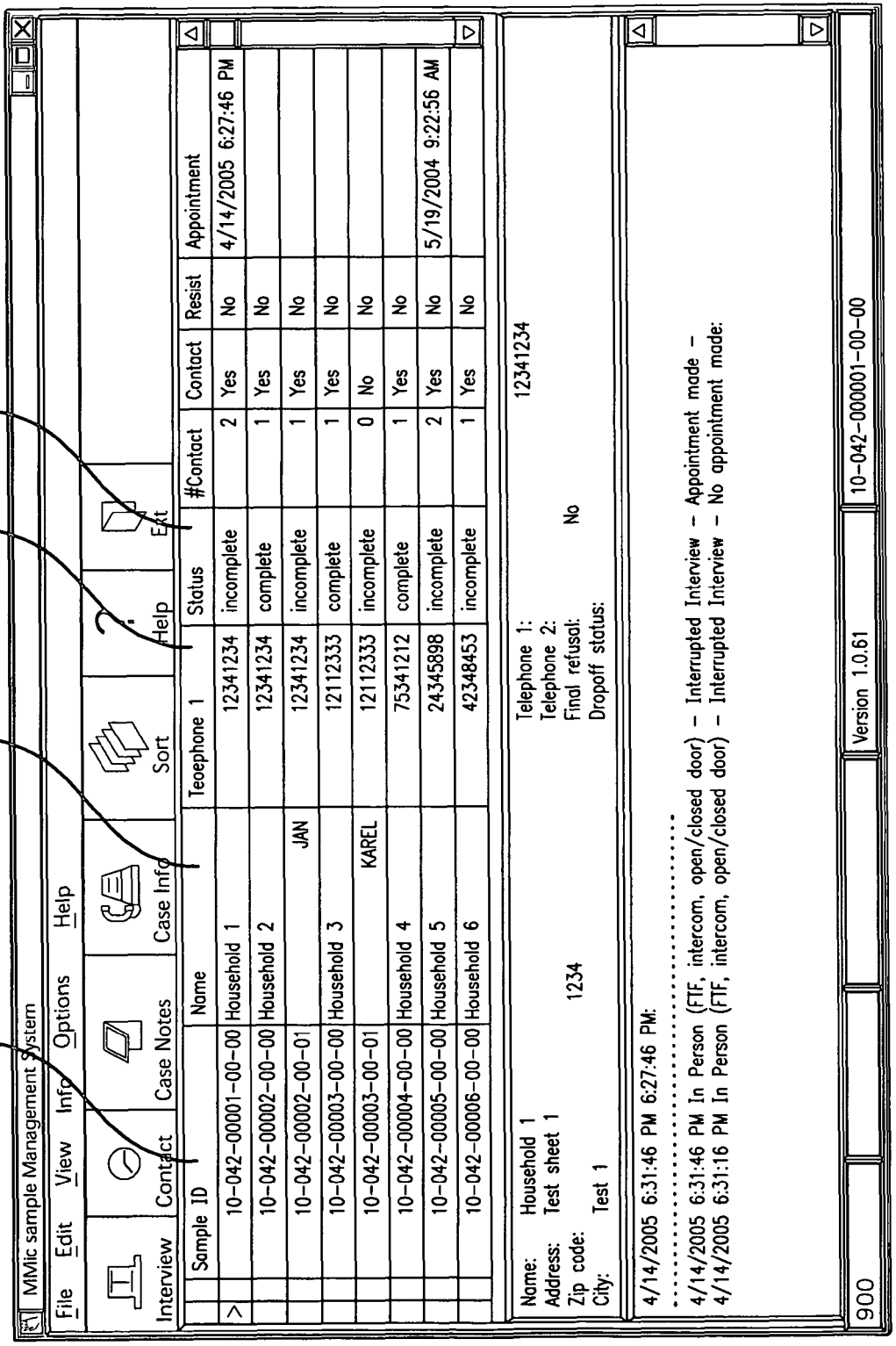
FIG. 9 is a screen dump of a typical MMIC sample management system.

Reference should now be made to FIG. 9, which is a screen dump of a typical MMIC sample management system. A survey involves a number of questions each directed to a statistically meaningful set 56 (a "sample") of respondents 58 selected from a larger universe of potential respondents. Managing a sample is a vital part of any efficient survey, in order to issue calls and determine what to do with each sample record. A sample consists of potential respondents in the form of several individual records 60. The records are made up of many variables. Record variables store information about each record, such as telephone number 62, name 58, language spoken, or postal code. The sample is loaded into the Sample Management System ("SMS") and held in a table 64 in a database.

In the tables, the SMS stores the records it reads from the sample files. Once a sample has been loaded, it remains in the SMS and records are moved from table to table according to their current status 66 and rules that determine the selection of a record and its disposition once the interview has been completed. Although these are the most important functions, many other rules can be defined as well. These might include custom reports, automatic sample loads, or periodical printouts of appointment schedules.

Global characteristics of the study usually set the standards or limits for the study as a whole. For instance, a study variable might be set to define the maximum number of attempts allowed per record, or to indicate the time delay required before calling back busy numbers. The values of study variables are not permanent, and supervisors with the proper permissions can change them at any time while interviewing is in progress, without changing the SMS algorithms.

Meta Data and Report Module

Figure 10:
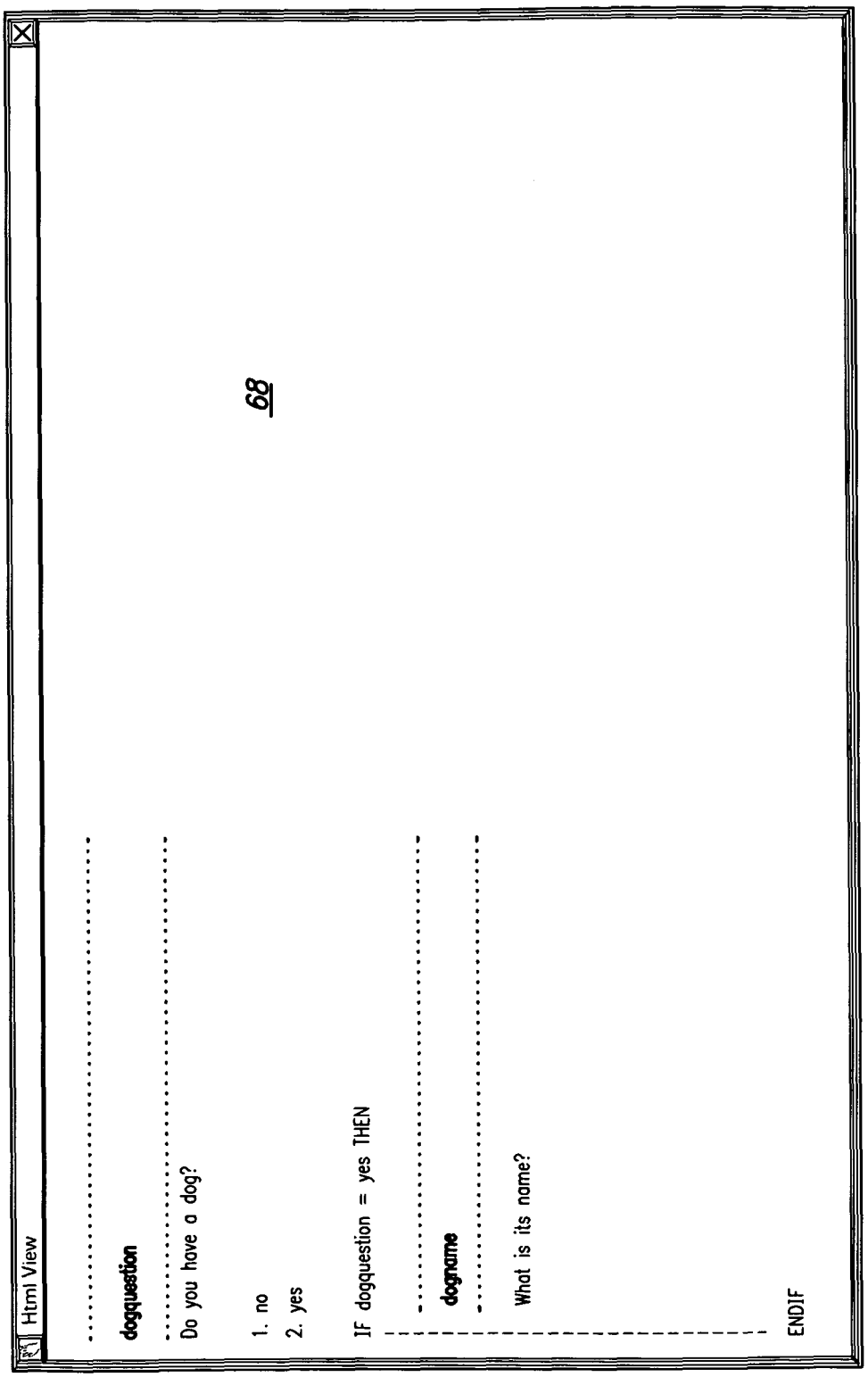
FIG. 10 is a screen dump of an exemplary MMIC meta data viewer.

As shown in FIG. 10, Meta data 68 describes the content and the flow of the questionnaire. Possible tools for meta data descriptions include programs for the generation of a paper version of the questionnaire and an overview of variables and questions used in the survey.

Datamodel Object

FIG. 11 shows some of the most important structures of the main MMIC Datamodel Object 24. When a question is programmed, the properties of this question (called a "field" in the MMIC programming language), such as "question text" and "name", are accessible from any point in the survey and not just when it appears on the route during an interview. It is possible to browse through all the conditions in the questionnaire and directly link to questions involved in the conditions. These links are stored in the form of pointers to Field Objects 70. The actual field (question) is stored only once in the Datamodel Object as a Field Object. A Field Object can operate in different ways in a survey. It can act like a variable in conditions or assignments, but it can also act as a procedure call (function) to display a question text on the screen and to store an answer given by the respondent or interviewer. The MMIC Field Object is described in more detail hereinafter with reference to FIG. 12.

The light gray (striped) boxes in this structure represent lists of objects. So, the Fields box may point to one or more fields (questions) that are asked in the questionnaire and/or to fields (assignments) that have values that are automatically assigned (such as the date and time of the survey).

The Rules list describes the flow of the questionnaire, and in effect constitutes a blue print of the possible events during a survey. The Rules list consists of statements, conditions (conditional logic), and checks.

Statement Object 74 represents an assignment or question (which act like executable command lines) in the survey. A statement can be either the fact that a question is being asked (in this case the field is used as a function), or an assignment to a field (for example to set the time that the survey started), or the monthly income of a respondent in case the income was given on a yearly base (here the field is used as a variable).

The Condition Object 76 represents the conditional logic under which a Statement Object is executed. Conditions (conditional logic) determine whether a question is asked or not. If there is a series (block) of questions about someone's children, the respondent might not be asked if a question before the series of children questions asks the respondent whether he/she has any children, and the response is "no". The series of children questions can be restricted by a condition based on this question about having any children at all. Conditions are stored in a Condition Object. Checks are a somewhat more complex form of conditional logic that does more than simply examine prior responses to determine whether or not a specific question (or series of questions) should be asked, but rather analyzes the current response for possible inconsistencies with prior responses, and, if a possible inconsistency is detected, issues a warning or error message to the interviewer and/or provides the respondent with an opportunity to revise or expand on that response. A typical example is when someone answers that he/she is married and also that he/she is only 12 years old. In that case, a researcher might want an error message to appear that will suggest changing one of the answers.

Next to the Field lists 80 and the Rules lists 72, there are a number of other properties that can be set and retrieved from the Datamodel Object 24, such as a Name 82 and a Description 84 for the survey. For Name and Description the respective functions used to retrieve their respective properties are getName( ) and getDescription( ). These properties can point to complex objects such as the Field Object, but also to straightforward objects such as a simple object to store a text (string). Other important properties and lists on the Datamodel level include the Layout Object 86 and the Database Object 26 (which controls the storage of given answers and assignments).

Not all properties need to be defined in order to run a survey. For example, one could choose not to add a description to a questionnaire. However, in order to conduct a meaningful survey with a non-trivial MMIC function, the Datamodel Object 24 should have at least some fields with assigned values and also should have rules that describe how at least some of those assignments are determined dynamically as the survey is being conducted.

Field Object

Field Objects 70 are the basic building blocks of any questionnaire. They are locations in the database that may be filled with data (such as questions, responses to questions, or other information that is automatically assigned based on prior responses or other known data. As discussed earlier, a field can perform different programming roles. The Field Object can be used to store data by asking a question and accepting a response (using it as a procedure or function), or it can be assigned a value without asking a question (using it as an assignment or variable).

Below is an example where three Fields 'Incomequestion', 'Yearlyincome' and 'Monthlyincome' are potential questions.

Incomequestion
"Do you want to give answers to income questions on a per year or per month base?": (year, month)
Yearlyincome
"What is your yearly income in dollars?": 0.10000000
Monthlyincome
"What is your monthly income in dollars?": 0.10000000

The routing ("Rules") section determines whether which of these Fields are going to be asked of the respondent and which will be calculated ("Assigned") without necessarily explicitly presenting them to the respondent or interviewer.

```
Incomequestion
if Incomequestion = year then
    Yearlyincome
    Monthlyincome := Yearlyincome / 12
else
    Monthlyincome
    Yearlyincome := Monthlyincome * 12
endif
```

In the foregoing example, the 'Incomequestion' is always asked of the respondent. Depending on the answer given, the follow-up 'Yearlyincome' and 'Monthlyincome' are either asked or assigned to. If the respondent answers 'year' then the 'Yearlyincome' is asked and the 'Monthlyincome' is calculated and assigned by dividing the answer given to 'Yearlyincome' by 12.

Figure 12:
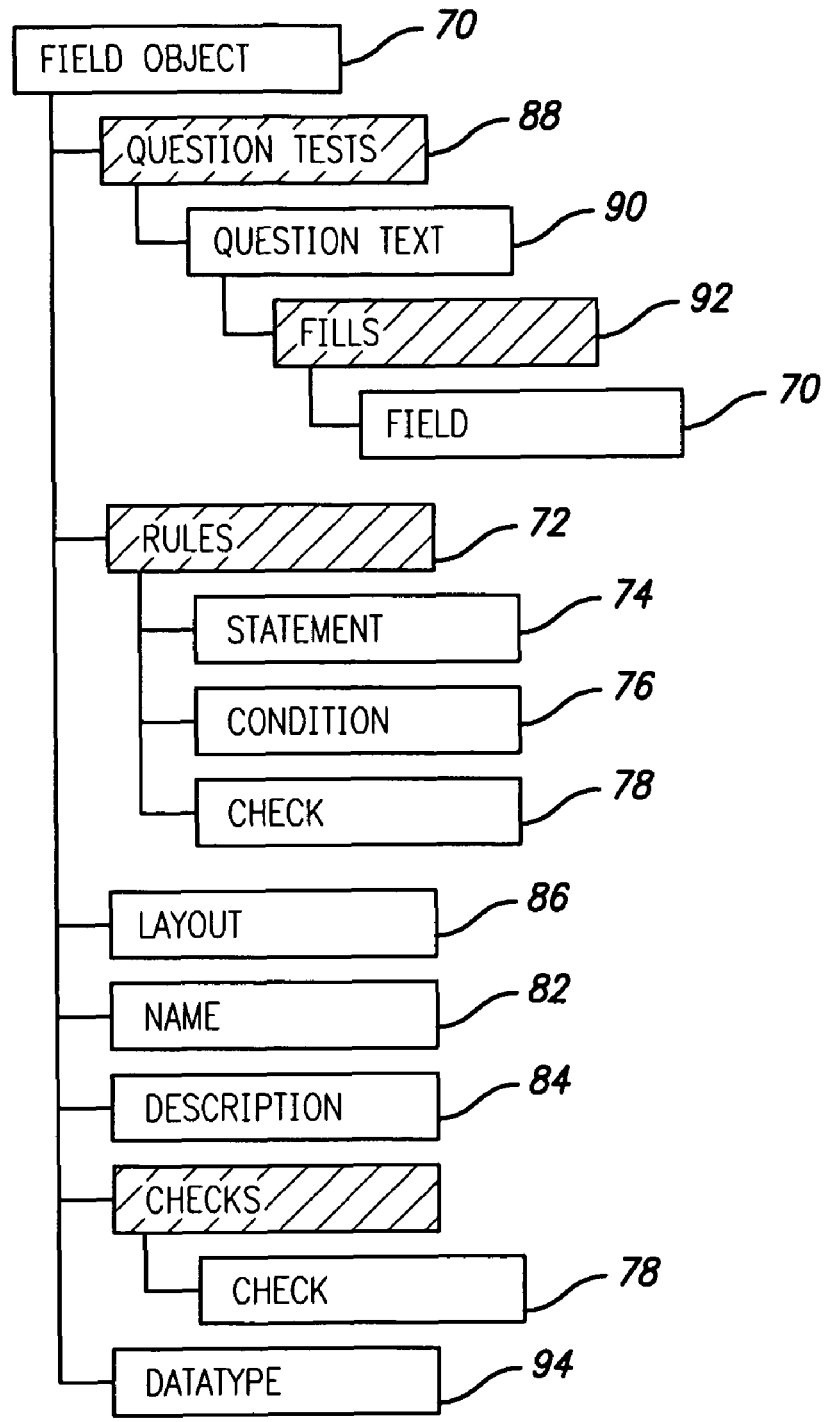
FIG. 12 shows some of the basic components of an exemplary Field Object.

FIG. 12 shows some of the basic components of a Field Object 70. Every field can include an associated list 88 of QuestionText Objects 90. A Field Object can have a QuestionText Object 90 assigned to it for every language defined on the Datamodel Object level. For example, a survey that is conducted in the English and Spanish language has two QuestionText Objects in the "QuestionText" list on the Field Object level, both associated with Fills 92 (Fields 70 that represent responses recorded by the interviewer and/or other data objects that supplement or respond to the associated QuestionText Object 90). Alternatively, the Field Object 70 can be a calculated or assigned field (for example, a GPS location) and this Field Object 70 may have a Name 82 and a Description 84 property, but no actual question text and thus an empty Question Text Object associated with it. Question Texts Objects can also hold Fills 92, which include references to other Field Objects 70. This makes it possible to show personalized question texts based on previous answers or preloaded data. These referenced Field Objects may be no different in structure from normal Field Objects. FIG. 14 includes a detailed example of a fill.

Every field has one or more statements (rules) assigned to it. A question that is asked only once in the questionnaire has only one statement. The statement in this case will simply signify that the question is being asked of the respondent. More complicated assignments (calculations) have multiple Statement Objects assigned to them. These statements appear on the Datamodel Object level together with all the other statements in the survey and on the Field Object level together with all the other statements that are involved in that particular field.

Another list on the Field Object 70 level is the Rules list 72. It contains the complete list of all the logical conditions 76 that are involved in 'getting to' a particular field in the questionnaire. If there is a question text (question) that is asked of a certain subgroup of the sample, the conditions that are stored in this structure are the ones that must be satisfied before that question is asked.

The Field Object 70 holds properties for the Name 82 and Description 84 of an associated question as well as a reference to the Datatype Object 94, which describes the data the field can contain. The Datatype Object will be described later with reference to FIG. 13.

Four important functions in the Field Object handle the storage and retrieval of the data. Each Field Object has a getText( ) and setText( ) function as well as a getFieldStatus( ) and setFieldStatus( ) function. The text functions store the actual data entered by the respondent or interviewer, where the Field Object status functions determine the type of answer given. In a case where the respondent refuses to answer a question, the text will generally be empty and the Field Object status will be set to "refuse". Data entered into the object is stored in an external database such as Oracle or mySQL. Next to the value and status some more information is stored in the database on a per field base. This information includes the date and time of the entry, the language in which this question was asked, the interviewing mode (web interview, telephone interview, etc.) and the version of the Datamodel in which the question was asked. This information allows researchers to later trace back the exact conditions under which this particular answer was given. This is important in case the survey was designed to be conducted in multiple modes, allowing the respondent to choose the mode or even combine modes, for example having telephone follow up questions for a web based interview. In this case, the researcher will always know in what mode each question was answered and even what part of the routing was 'opened up' by switching modes. The researcher can even force new questions to be asked of a respondent by switching modes and assigning an (new) interview for this respondent on the telephone or other mode. The data collected is independent of the modes and will all be stored in the same (external) database.

Datatype Object

Figure 13:
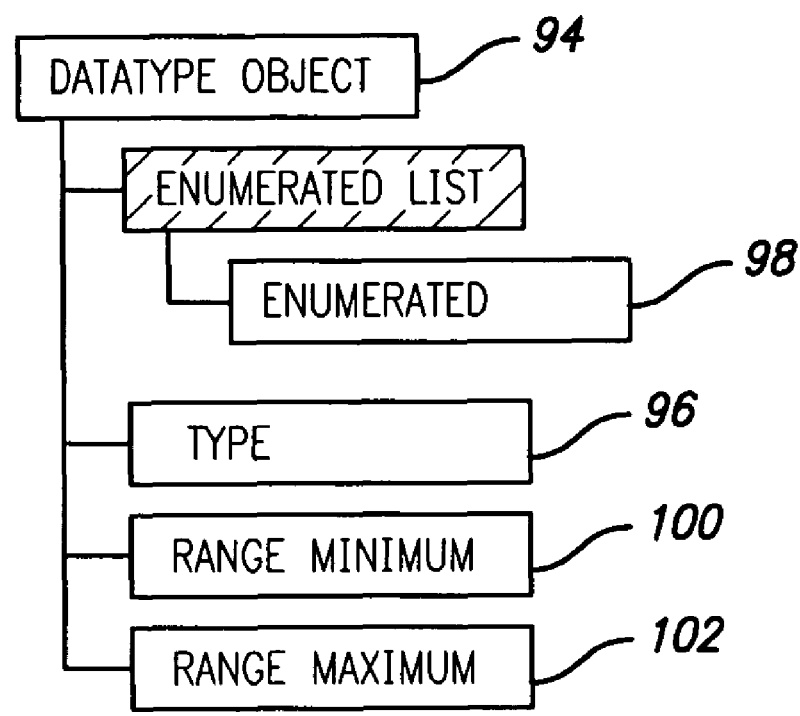
FIG. 13 shows how the Datatype Object of FIG. 11 describes the type of data to be stored for a specific Field Object.

As shown in FIG. 13, the Datatype Object 94 describes the Type 96 of data to be stored for a specific Field Object 70. Some of the possible types are: String (text), Integer (numbers) or Enumerated. Enumerated types consist of a list 98 of possible answers 98. An easy yes-no question is a simple Enumerated Datatype Object with only two possible answers: "Yes" or "No". When the Datatype is Integer, a Range minimum 100 and Range maximum 102 may be specified. An optional Attributes Object (not shown) can be provided on the Datamodel or Field Object level. In addition to a direct answer, respondents are sometimes allowed to answer refusal or don't know to a question or leave a question empty (no answer at all). These attributes can be set per question, block (set of questions) or Datamodel. Accessing the Attributes Object for a field tells the programmer what the answer options are for that specific question.

The Datatype Object 94 also supports the combination of answer types. In a question about age, one would typically allow a range from 0.120. The type property 96 in the Datatype Object in this case will return 'Integer', with a range minimum 100 of 0 and a range maximum 102 of 120. Datatype Objects can also be assigned to the Datamodel Object, acting as a global answer type that can be used for all underlying Field Objects.

Layout Object

The Layout Object 86 is another important part of the Datamodel and Field Object. It describes the look and feel of the question on the screen. Not only the color and the font of the question text are described here, but also the location on the screen, and the position of other possible questions or items (such as movies or images) on the same screen. Note that the Datamodel Layout Object determines a generic (default) appearance (FIG. 11), which can be modified by the corresponding Layout Object of a specific Field Object (FIG. 12).

Creating a Datamodel Object

The Datamodel Object contains functions to fill the object with questions and rules, such as Conditions, Statements, Assignments and (Data) Checks. In order to conduct a survey, information needs to be fed into the object using functions such as: addField( ), setQuestionText( ), addRule( ), etc. At the moment, MMIC uses a parser to navigate through a piece of text, allowing for a more convenient way for programmers to define a questionnaire using a predefined language structure, without needing to write a program that directly uses the MMIC functions. This principle is used in most other programming languages. Currently, MMIC supports the Blaise programming language as input, but we are also planning to support the CASES survey programming language. In addition to the CASES language structure, MMIC plans to implement two more convenient ways of designing a questionnaire: A web interface and a more graphically oriented interface. The web interface can be used for simple questionnaires and questionnaires where more languages are involved. It allows researchers and translators to directly access the texts used in the questions without inadvertently corrupting any associated routings and checks. The graphical user interface supports a more visual way of designing a questionnaire. Questions are displayed as boxes and arrows that represent the internal relationship between questions, showing paths and conditions in the questionnaire. The program then converts the boxes and arrows to the functions used in the MMIC Datamodel Object. All these programming interfaces use the same functions (addField( ), SetQuestionText( ), etc.) to fill the MMIC Datamodel Object.

On the data input side of the survey process, a program retrieves the information stored in the MMIC Datamodel Object in order to display questions on the screen and allow respondents or interviewers to enter data (answers) into the Object. There are many known ways and modes to display questions and record answers during the course of an interview. The MMIC data entry program that retrieves the question text is able to support many of these modes. It can display questions on a screen in a telephone room, allowing interviewers to conduct interviews over the phone, and it can also show questions on the Internet or PDAs to allow self-interviewing. Printing a paper version of the questionnaire is also contemplated, which will provide a hard copy that can be sent out by regular mail to the respondents.

Once the data is entered into the MMIC Object, it can be retrieved using the Database Object connected to the Datamodel Object or directly from the Database in which the data was stored. If the MMIC Object is used to retrieve the data, the users will be able to access all the meta data (Conditions, Statements, Checks, Description) connected to the particular Field associated with the data that is requested.

Example of Complicated Fill Routing

FIG. 14 shows the source code for a rather complicated example of the use of a fill in a question text. The code is written in the Blaise programming language. The MMIC survey program preferably includes the capability to read the source code file from multiple other survey programming languages such as Blaise and CASES. The question text of Field 'q3' contains a fill, in this case a reference to the field 'HWP', which will appear in the question text for the interviewer or respondent as 'your husband/wife' in case the respondent is married. The route to these fills is fairly complicated and leads through the function 'HWPfill'. During run time, this function is analyzed step by step as it comes up as Statements and conditions during the interview process. The decision process during interviewing is rather simple. We start with the first Statement. If this is a question, put the question on the screen and continue analyzing the next Statement or condition until we reach a question again. When a condition is reached, analyze the condition expression and go either into the 'then' part of the condition (in case the expression equals true) or the 'else' part of the condition. If we follow these simple rules, we will end up with a filled field for 'HWP'. When the question that uses this fill is supposed to be shown on the screen, we simply take the value for this field and replace them with the field name in the question text.

The MMIC Engine retrieves the value for the fills in question text at run time from the Database Object. At design and compile time however, all the possible paths to the Fill Field Object are stored and accessible through the Field, Statements and Conditions Object blocks. This allows for a get-PossibleFill( ) function which retrieves all possible Statements that can influence the outcome of the Fill on the screen. From a meta data point of view (see FIG. 10), this is extremely useful to both the programmer (during design and debug) and to the researcher (during validation and analysis).

Continuous Data Collection

The MMIC Engine is able to run and gather information without actually asking any questions. A typical survey guides a respondent or interviewer through a path of questions until the last question is asked. MMIC is able to run without conventional text-based questions and to gather data without the need of respondent interaction. One illustrative example of where and how MMIC can be used is in the television and radio audience measurement Field. MMIC could operate silently in the background and record all the channels that are being watched, and even pop up some questions on the television when a certain show in on. Another similar example is that MMIC can follow Internet browsing behavior and pop up questions in the browser when the user performs certain activities, such as searches for specific pages.

Screen Dumps of Some of the MMIC Components

Possible Extensions and Variations

Those skilled in the art will undoubtedly recognize that the described embodiments can be assembled in various ways to form a variety of applications based on the need, and that obvious alterations and changes in the described structure may be practiced without departing meaningfully from the principles, spirit and scope of this invention.

For example, MMIC could be provided with a web-based programming interface that displays a questionnaire generator on the web, allowing users to click together a simple questionnaire without the use of (or indeed, any knowledge of) the MMIC programming language. Such a web-based interface could then create and compile a MMIC Object by assigning fields and routing (conditions, statements and checks) directly to the Datamodel Object, which could be subsequently decompiled into any supported source code (for example, Blaise or Cases), even though it was created on the web. This decompiled source code could then be altered (perhaps with the original text of questions and interviewer prompts translated into another language) using the particular programming language appropriate for the resultant decompiled source code and recompiled again. Alternatively, such a web-based program interface could be used to translate or modify a MMIC Object that was originally compiled using any supported programming language and then decompiled into a format compatible with the web program.

As another example, MMIC could be provided with dynamic bidirectional linkages between the Engine, the Programming Interface, and the Interview Interface. At any time during the running of a survey program, the programmer could jump from the current program display to the corresponding line in the source code and then step through the different lines while viewing the corresponding actions in the survey process.

Accordingly, these and other alterations and changes should not be construed as substantial deviations from the present invention as set forth in the appended claims.

The invention claimed is:

1. A system on at least one computer having one or more processors, the system for conducting a survey questionnaire comprising:
an Engine module, controlled by the one or more processors of the least one computer, for assembling a datamodel object used to conduct a survey questionnaire, said datamodel object including a question section and a rule section, the question section having a plurality of question objects each comprising a question, the rule section having a plurality of rule objects for determining which questions of the question objects to present and the order in which to present the questions;
a programming interface controlled by the one or more processors of the least one computer, the programming interface coupled to the Engine module, the programming interface for defining the plurality of questions of the datamodel object,
the programming interface further comprising a metadata viewer for allowing access to metadata while the plurality of questions and the rules are defined at the programming interface;
a data storage module controlled by the one or more processors of the least one computer, the data storage module external from the Engine module, the data storage module for storing the datamodel object assembled by the Engine module, wherein the question objects are stored in a separate portion of the data storage module from the rule objects;
the Engine module comprising a database object module for sharing data with the data storage module; and
an interview interface coupled to the Engine module, the interview interface for presenting questions from the datamodel object stored on the external data storage module to an interview subject;
wherein:
the Engine module is for receiving, from the interview interface, a response to a question presented to the interview subject;
the database object module is for storing, to the data storage module, the response of the interview subject received by the Engine module and response metadata associated with the response; and
the Engine module is for outputting a subsequent question of the question objects from the data storage module to the interview interface, based on the rule objects and the responses of the interview subject stored in the data storage module.

2. A system on at least one computer having one or more processors, the system for conducting a survey questionnaire comprising:
a programming interface, controlled by the one or more processors of the least one computer, for defining model information for conducting a survey questionnaire, the model information including a question section and a rule section, the question section having a plurality of question objects each comprising a question, the rule section having a plurality of rule objects for determining which questions to present and the order in which to present the questions;
an Engine module, controlled by the one or more processors of the least one computer, for assembling a datamodel object based on the model information defined with the programming interface;
a database object module controlled by the one or more processors of the least one computer, the database object module associated with the Engine module, the database object module for sharing data with a data storage module external from the Engine module, the database object module for storing the datamodel object assembled by the Engine module in the data storage module, wherein the question objects are stored in a separate portion of the data storage module from the rule objects;
the Engine module associated with an interview interface for presenting questions based on the database object module, stored on the data storage module, to an interview subject;
the Engine module for receiving, from the interview interface, a response to a question presented to the interview subject;
the database object module for storing, to the data storage module, the response of the interview subject received by the Engine module and response metadata associated with the response;
the Engine module for outputting a subsequent question of the question objects from the data storage module to the interview interface, based on the rule objects and the responses of the interview subject stored in the data storage module.

3. The system of claim 2, wherein the programming interface defines a layout format for the interview interface.

4. The system of claim 2, wherein the programming interface includes a parser for a text based survey programming language.

5. The system of claim 4, wherein the programming interface supports the Blaise programming language and at least one other text based survey programming language.

6. The system of claim 2, wherein the programming interface supports at least one of a web-based survey language and a graphical programming language.

7. The system of claim 2, wherein the interview interface supports at least one computer assisted interviewing mode selected from the group consisting essentially of CATI (Computer Assisted Telephone Interviewing) and CAPI (Computer Assisted Personal Interviewing).

8. The system of claim 7, wherein the interview interface supports more than one computer assisted interviewing mode.

9. The system of claim 2, wherein the interview interface supports telephone interviewing, written interviewing, and personal interviewing.

10. The system of claim 2, wherein:
the datamodel object includes Field objects, QuestionText objects, Statement objects, and Condition objects;
each response stored in the data storage module is associated with a corresponding Field object and respondent;
at least some of the associated Field objects include one or more QuestionText objects, one or more Statement objects, and one or more Condition objects;

the Statement objects define permissible routings from a particular Field object to one or more subsequent Field objects;

the Condition objects define permissible routings to a particular Field object from one or more previous Field objects;

each response stored in the data storage module includes a reference to the QuestionText object which elicited the response and a reference to context of the response.

11. The system of claim 10, wherein:

the permissible routings are combinable into a recursive routing in which the same Field object and its associated QuestionText is presented more than once during the presentation of the questionnaire to the same respondent.

12. The system of claim 10, wherein said context includes a reference to the specific routing to the referenced QuestionText object.

13. The system of claim 12, wherein said specific routing includes at least one Field object selected from Statement objects and Condition objects.

14. The system of claim 2, wherein the Engine module switches from one language to another language during run time.

15. The system of claim 2, wherein the programming interface defines a database format for the data storage module.

16. The system of claim 2, the programming interface comprising:

a metadata viewer for allowing access to metadata while model information is being defined on the programming interface.

17. The system of claim 2, wherein the interview interface is external the Engine module.

18. The system of claim 2, wherein the response metadata comprises one or more links from one or more questions and responses that lead to said response.

19. The system of claim 2, the rule objects of the datamodel object including checks to provide an indication to the interview interface that a response to a question is inconsistent with at least one of previous responses and non-textual data relating to the interview.

20. The system of claim 2, the Engine module for outputting the subsequent question from the data storage module to the interview interface, based on the rule objects of the datamodel object, the responses of the interview subject stored in the data storage module, and non-textual electronic data collected from the interview subject.

21. The system of claim 20, wherein the non-textual electronic data comprises internet browsing behavior of the interview subject.

22. The system of claim 20, wherein the non-textual electronic data comprises biomarker data.

23. The system of claim 20, wherein the non-textual electronic data is collected without human interaction.

24. The system of claim 2, the Engine module for outputting the subsequent question from the data storage module to the interview interface, based on the rule objects of the datamodel object, the responses of the interview subject stored in the data storage module, and non-textual electronic data collected during an interview of the interview subject.

25. The system of claim 2, the Engine module for outputting the subsequent question from the data storage module to the interview interface, based on the rule objects of the datamodel object, the responses of the interview subject stored in the data storage module, and non-textual electronic data collected before an interview of the interview subject.

26. The system of claim 2, the Engine module for outputting the subsequent question from the data storage module to the interview interface, based on the rule objects of the datamodel object, the responses of the interview subject stored in the data storage module, and values calculated based upon the responses of the interview subject stored in the data storage module.

27. The system of claim 2, wherein the program tool is platform independent.

28. The system of claim 2, wherein the question objects are defined independently of the rule objects.

29. The system of claim 2, the rule objects including a set of conditions for each question that must be satisfied before a question is presented from among the plurality of questions.

30. The system of claim 2, the data storage module having a first portion and a second portion separate from the first portion, the first portion for storing the question section of the data model object, the second portion for storing the rule section of the data model object.

31. The system of claim 2, wherein the question objects of the datamodel object are organized in a relational structure such that a particular question is accessed from more than one previous question and in which the particular question leads to more than one subsequent question.

32. The system of claim 31, wherein the relational structure permits the particular question to be accessed more than once during the same interview.

33. The system of claim 32, wherein the relational structure allows the particular question to lead recursively to the particular question.

34. The system of claim 2, wherein responses to previous questions that are stored on the data storage module are not provided to the interview interface along with the questions.

35. The system of claim 2, the Engine module for receiving the response without the question for which the response is provided by the interview subject.

36. The system of claim 2, the Engine module for outputting the subsequent question without the response that lead to the subsequent question.

* * * * *